United States Patent [19]

Giordano

[11] Patent Number: 5,457,049

[45] Date of Patent: Oct. 10, 1995

[54] TUMOR SUPPRESSOR PROTEIN PRB2, RELATED GENE PRODUCTS, AND DNA ENCODING THEREFOR

[75] Inventor: Antonio Giordano, Willow Grove, Pa.

[73] Assignee: Temple University - of the Commonwealth System of Higher Education, Philadelphia, Pa.

[21] Appl. No.: 106,493

[22] Filed: Aug. 12, 1993

[51] Int. Cl.⁶ .................. C12N 1/21; C12N 15/12; C12N 15/70

[52] U.S. Cl. .................. 435/252.33; 435/252.3; 435/320.1; 435/172.3; 435/91.1; 435/849; 536/23.1; 536/23.5; 530/350; 935/9; 935/29; 935/73

[58] Field of Search .................. 435/320.1, 252.3, 435/252.83, 91.1, 91.4, 91.41; 536/23.1, 23.5; 935/9, 11, 22, 29, 56, 60, 73

[56] References Cited

U.S. PATENT DOCUMENTS

4,675,285  6/1987  Clark et al. .................. 435/6

OTHER PUBLICATIONS

Kaelin et al. 1990 Molec. Cell. Biol. 10, 3761–3769.
Mayol et al. 1993 Oncogene 8, 2561–2566.
Watson, J. D. 1987, in: *Molecular Biology of the Gene*. Benjamin/Cummings Publ. Co. Inc. Menlo Park, Calif. p. 313.
Webster's II. New Riverside University Dictionary. Houghton Mifflin Co., Boston, Mass. p. 1279, Published 1984.
Li, et al. 1993, Genes and Development. 7, 2366–2377.
Dyson et al. 1992, J. Virol. 66, 6893–6902.
Stratagene Catalog 1989, pp. 34–37.
Stratageni Catalog 1993 pp. 38, 39, 304–307.
Cobrinik et al., "Identification of a 126 kD E1A-Binding Protein That Forms G0/G1 Complexes with E2F," presented at Hood College, Frederick, Md., Ninth Annual Meeting on Oncogenes (Jun. 1992).
Robert A. Weinberg, "Tumor Suppressor Genes," *Science*, vol. 254, pp. 1138–1146 (Nov. 1991).
Giordano et al., "Human Cyclin A and the Retinoblastoma Protein Interact with Similar but Distinguishable Sequences in the Adenovirus E1A Gene Product," *Oncogene* 6, 481–485 (1992).
Ewen et al., "Molecular Cloning, Chromosomal Mapping, and Expression of the cDNA for p107, a Retinoblastoma Gene Product–Related Protein," *Cell*, vol. 66, pp. 1155–1164 (Sep. 1991).
Lee et al., "Human Retinoblastoma Susceptibility Gene: Cloning, Identification, and Sequence," *Science*, vol. 235, pp. 1394–1399 (Mar. 1987).

*Primary Examiner*—Christopher S. F. Low
*Attorney, Agent, or Firm*—Seidel Gonda Lavorgna & Monaco

[57] ABSTRACT

The invention provides a tumor suppressor protein of the retinoblastoma family (pRb2) which binds to the E1A transforming domain and to DNA encoding for the pRb2 protein.

8 Claims, 2 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 3249 base pairs
( B ) TYPE: nucleic acid
( C ) STRANDEDNESS: Single -continued ( D ) TOPOLOGY: linear ( x i ) SEQUENCE DESCRIPTION: SEQ ID NO:1:

| | | | | | |
|---|---|---|---|---|---|
| ATGGACGAGG | CGGCGCGGGC | CGAGGCCTGG | GACAGCTACC | GCAGCATGAG | 50 |
| CGAAAGCTAC | ACGCTGGAGG | GAAATGATCT | TCATTGGTTA | GCATGTGCCT | 100 |
| TATATGTGGC | TTGCAGAAAA | TCTGTTCCAA | CTGTAAGCAA | AGGGACAGTG | 150 |
| GAAGGAAACT | ATGTATCTTT | AACTAGAATC | CTGAAATGTT | CAGAGCAGAG | 200 |
| CTTAATCGAA | TTTTTAATA | AGATGAAGAA | GTGGGAAGAC | ATGGCAAATC | 250 |
| TACCCCCACA | TTTCAGAGAA | CGTACTGAGA | GATTAGAAAG | AAACTTCACT | 300 |
| GTTTCTGCTG | TAATTTTTAA | GAAATATGAA | CCCATTTTTC | AGGACATCTT | 350 |
| TAAATACCCT | CAAGAGGAGC | AACCTCGTCA | GCAGCGAGGA | AGGAAACAGC | 400 |
| GGCGACAGCC | CTGTACTGTG | TCTGAAATTT | CCATTTTTG | TTGGATGCTT | 450 |
| TTTATATATG | CAAAAGGTAA | TTTCCCCATG | ATTAGTGATG | ATTTGGTCAA | 500 |
| TTCTTATCAC | CTGCTGCTGT | GTGCTTTGGA | CTTAGTTTAT | GGAAATGCAC | 550 |
| TTCAGTGTTC | TAATCGTAAA | GAACTTGTGA | ACCCTAATTT | TAAAGGCTTA | 600 |
| TCTGAAGATT | TTCATGCTAA | AGATTCTAAA | CCTTCCTCTG | ACCCCCCTTG | 650 |
| TATCATTGAG | AAACTGTGTT | CCTTACATGA | TGGCCTAGTT | TTGGAAGCAA | 700 |
| AGGGGATAAA | GGAACATTTC | TGGAAACCCT | ATATTAGGAA | ACTTTATGAA | 750 |
| AAAAAGCTCC | TTAAGGGAAA | AGAAGAAAAT | CTCACTGGGT | TTCTAGAACC | 800 |
| TGGGAACTTT | GGAGAGAGTT | TTAAAGCCAT | CAATAAGGCC | TATGAGGAGT | 850 |
| ATGTTTATC | TGTTGGGAAT | TTAGATGAGC | GGATATTTCT | TGGAGAGGAT | 900 |
| GCTGAGGAGG | AAATTGGGAC | TCTCTCAAGG | TGTCTGAACG | CTGGTTCAGG | 950 |
| AACAGAGACT | GCTGAAAGGG | TGCAGATGAA | AAACATCTTA | CAGCAGCATT | 1000 |
| TTGACAAGTC | CAAAGCACTT | AGAATCTCCA | CACCACTAAC | TGGTGTTAGG | 1050 |
| TACATTAAGG | AGAATAGCCC | TTGTGTGACT | CCAGTTTCTA | CAGCTACGCA | 1100 |
| TAGCTTGAGT | CGTCTTCACA | CCATGCTGAC | AGGCCTCAGG | AATGCACCAA | 1150 |
| GTGAGAAACT | GGAACAGATT | CTCAGGACAT | GTTCCAGAGA | TCCAACCCAG | 1200 |
| GCTATTGCTA | ACAGACTGAA | AGAAATGTTT | GAAATATATT | CTCAGCATTT | 1250 |
| CCAGCCAGAC | GAGGATTTCA | GTAATTGTGC | TAAAGAAATT | GCCAGCAAAC | 1300 |
| ATTTTCGTTT | TGCGGAGATG | CTTTACTATA | AGTATTAGA | ATCTGTTATT | 1350 |
| GAGCAGGAAC | AAAAAAGACT | AGGAGACATG | GATTTATCTG | GTATTCTGGA | 1400 |
| ACAAGATGCG | TTCCACAGAT | CTCTCTTGGC | CTGCTGCCTT | GAGGTCGTCA | 1450 |
| CTTTTTCTTA | TAAGCCTCCT | GGGAATTTTC | CATTTATTAC | TGAAATATTT | 1500 |
| GATGTGCCTC | TTTATCATTT | TTATAAGGTG | ATAGAAGTAT | TCATTAGAGC | 1550 |
| AGAAGATGGC | CTTTGTAGAG | AGGTGGTAAA | ACACCTTAAT | CAGATTGAAG | 1600 |
| AACAGATCTT | AGATCATTTG | GCATGGAAAC | CAGAGTCTCC | ACTCTGGGAA | 1650 |
| AAAATTAGAG | ACAATGAAAA | CAGAGTTCCT | ACATGTGAAG | AGGTCATGCC | 1700 |
| ACCTCAGAAC | CTGGAAAGGG | CAGATGAAAT | TTGCATTGCT | GGCTCCCCTT | 1750 |
| TGACTCCCAG | AAGGGTGACT | GAAGTTCGTG | CTGATACTGG | AGGACTTGGA | 1800 |
| AGGAGCATAA | CATCTCCAAC | CACATTATAC | GATAGGTACA | GCTCCCCACC | 1850 |
| AGCCAGCACT | ACCAGAAGGC | GGCTATTTGT | TGAGAATGAT | AGCCCCTCTG | 1900 |

-continued

```
ATGGAGGGAC ACCTGGGCGG ATGCCCCCAC AGCCCCTAGT CAATGCTGTC 1950
CCTGTGCAGA ATGTATCTGG GGAGACTGTT TCTGTCACAC CAGTTCCTGG 2000
ACAGACTTTG GTCACCATGG CAACCGCCAC TGTCACAGCC AACAATGGGC 2050
AAACGGTAAC CATTCCTGTG CAAGGTATTG CCAATGAAAA TGGAGGGATA 2100
ACATTCTTCC CTGTCCAAGT CAATGTTGGG GGGCAGGCAC AAGCTGTGAC 2150
AGGCTCCATC CAGCCCCTCA GTGCTCAGGC CCTGGCTGGA AGTCTGAGCT 2200
CTCAACAGGT GACAGGAACA ACTTTGCAAG TCCCTGGTCA AGTGGCCATT 2250
CAACAGATTT CCCCAGGTGG CCAACAGCAG AAGCAAGGCC AGTCTGTAAC 2300
CAGCAGTAGT AATAGACCCA GGAAGACCAG CTCTTTATCG CTTTTCTTTA 2350
GAAAGGTATA CCATTTAGCA GCTGTCCGCC TTCGGGATCT CTGTGCCAAA 2400
CTAGATATTT CAGATGAATT GAGGAAAAAA ATCTGGACCT GCTTTGAATT 2450
CTCCATAATT CAGTGTCCTG AACTTATGAT GGACAGACAT CTGGACCAGT 2500
TATTAATGTG TGCCATTTAT GTGATGGCAA AGGTCACAAA AGAAGATAAG 2550
TCCTTCCAGA ACATTATGCG TTGTTATAGG ACTCAGCCGC AGGCCCGGAG 2600
CCAGGTGTAT AGAAGTGTTT TGATAAAAGG GAAAAGAAAA AGAAGAAATT 2650
CTGGCAGCAG TGATAGCAGA AGCCATCAGA ATTCTCCAAC AGAACTAAAC 2700
AAAGATAGAA CCAGTAGAGA CTCCAGTCCA GTTATGAGGT CAAGCAGCAC 2750
CTTGCCAGTT CCACAGCCCA GCAGTGCTCC TCCCACACCT ACTCGCCTCA 2800
CAGGTGCCAA CAGTGACATG GAAGAAGAGG AGAGGGGAGA CCTCATTCAG 2850
TTCTACAACA ACATCTACAT CAAACAGATT AAGACATTTG CCATGAAGTA 2900
CTCACAGGCA AATATGGATG CTCCCCCACT CTCTCCCTAT CCATTTGTAA 2950
GAACAGGCTC CCCTCGCCGA ATACAGTTGT CTCAAAATCA TCCTGTCTAC 3000
ATTTCCCCAC ATAAAAATGA ACAATGCTT TCTCCTCGAG AAAAGATTTT 3050
CTATTACTTC AGCAACAGTC CTTCAAAGAG ACTGAGAGAA ATTAATAGTA 3100
TGATACGCAC AGGAGAAACT CCTACTAAAA AGAGAGGAAT TCTTTTGGAA 3150
GATGGAAGTG AATCACCTGC AAAAGAATT TGCCCAGAAA ATCATTCTGC 3200
CTTATTACGC CGTCTCCAAG ATGTAGCTAA TGACCGTGGT TCCCACTGA 3249
```

( 2 ) INFORMATION FOR SEQ ID NO:2:

( i ) SEQUENCE CHARACTERISTICS:
    ( A ) LENGTH: 1082 amino acids
    ( B ) TYPE: amino acid
    ( D ) TOPOLOGY: linear ( x i ) SEQUENCE DESCRIPTION: SEQ ID NO:2:

```
Met Asp Glu Ala Ala Arg Ala Glu Ala Trp Asp Ser Tyr Arg Ser
                 5                  10                  15
Met Ser Glu Ser Tyr Thr Leu Glu Gly Asn Asp Leu His Trp Leu
                20                  25                  30
Ala Cys Ala Leu Tyr Val Ala Cys Arg Lys Ser Val Pro Thr Val
                35                  40                  45
Ser Lys Gly Thr Val Glu Gly Asn Tyr Val Ser Leu Thr Arg Ile
                50                  55                  60
Leu Lys Cys Ser Glu Gln Ser Leu Ile Glu Phe Phe Asn Lys Met
                65                  70                  75
```

-continued

```
Lys Lys Trp Glu Asp Met Ala Asn Leu Pro Pro His Phe Arg Glu
            80                  85              90
Arg Thr Glu Arg Leu Glu Arg Asn Phe Thr Val Ser Ala Val Ile
            95                 100             105
Phe Lys Lys Tyr Glu Pro Ile Phe Gln Asp Ile Phe Lys Tyr Pro
           110                 115             120
Gln Glu Glu Gln Pro Arg Gln Gln Arg Gly Arg Lys Gln Arg Arg
           125                 130             135
Gln Pro Cys Thr Val Ser Glu Ile Phe His Phe Cys Trp Met Leu
           140                 145             150
Phe Ile Tyr Ala Lys Gly Asn Phe Pro Met Ile Ser Asp Asp Leu
           155                 160             165
Val Asn Ser Tyr His Leu Leu Leu Cys Ala Leu Asp Leu Val Tyr
           170                 175             180
Gly Asn Ala Leu Gln Cys Ser Asn Arg Lys Glu Leu Val Asn Pro
           185                 190             195
Asn Phe Lys Gly Leu Ser Glu Asp Phe His Ala Lys Asp Ser Lys
           200                 205             210
Pro Ser Ser Asp Pro Pro Cys Ile Ile Glu Lys Leu Cys Ser Leu
           215                 220             225
His Asp Gly Leu Val Leu Glu Ala Lys Gly Ile Lys Glu His Phe
           230                 235             240
Trp Lys Pro Tyr Ile Arg Lys Leu Tyr Glu Lys Lys Leu Leu Lys
           245                 250             255
Gly Lys Glu Glu Asn Leu Thr Gly Phe Leu Glu Pro Gly Asn Phe
           260                 265             270
Gly Glu Ser Phe Lys Ala Ile Asn Lys Ala Tyr Glu Glu Tyr Val
           275                 280             285
Leu Ser Val Gly Asn Leu Asp Glu Arg Ile Phe Leu Gly Glu Asp
           290                 295             300
Ala Glu Glu Glu Ile Gly Thr Leu Ser Arg Cys Leu Asn Ala Gly
           305                 310             315
Ser Gly Thr Glu Thr Ala Glu Arg Val Gln Met Lys Asn Ile Leu
           320                 325             330
Gln Gln His Phe Asp Lys Ser Lys Ala Leu Arg Ile Ser Thr Pro
           335                 340             345
Leu Thr Gly Val Arg Tyr Ile Lys Glu Asn Ser Pro Cys Val Thr
           350                 355             360
Pro Val Ser Thr Ala Thr His Ser Leu Ser Arg Leu His Thr Met
           365                 370             375
Leu Thr Gly Leu Arg Asn Ala Pro Ser Glu Lys Leu Glu Gln Ile
           380                 385             390
Leu Arg Thr Cys Ser Arg Asp Pro Thr Gln Ala Ile Ala Asn Arg
           395                 400             405
Leu Lys Glu Met Phe Glu Ile Tyr Ser Gln His Phe Gln Pro Asp
           410                 415             420
Glu Asp Phe Ser Asn Cys Ala Lys Glu Ile Ala Ser Lys His Phe
           425                 430             435
Arg Phe Ala Glu Met Leu Tyr Tyr Lys Val Leu Glu Ser Val Ile
           440                 445             450
Glu Gln Glu Gln Lys Arg Leu Gly Asp Met Asp Leu Ser Gly Ile
           455                 460             465
```

-continued

| | | | | | | | | | | | | |
|---|---|---|---|---|---|---|---|---|---|---|---|---|
| Leu | Glu | Gln | Asp | Ala 470 | Phe | His | Arg | Ser | Leu 475 | Leu | Ala | Cys | Cys | Leu 480 |
| Glu | Val | Val | Thr | Phe 485 | Ser | Tyr | Lys | Pro | Pro 490 | Gly | Asn | Phe | Pro | Phe 495 |
| Ile | Thr | Glu | Ile | Phe 500 | Asp | Val | Pro | Leu | Tyr 505 | His | Phe | Tyr | Lys | Val 510 |
| Ile | Glu | Val | Phe | Ile 515 | Arg | Ala | Glu | Asp | Gly 520 | Leu | Cys | Arg | Glu | Val 525 |
| Val | Lys | His | Leu | Asn 530 | Gln | Ile | Glu | Glu | Gln 535 | Ile | Leu | Asp | His | Leu 540 |
| Ala | Trp | Lys | Pro | Glu 545 | Ser | Pro | Leu | Trp | Glu 550 | Lys | Ile | Arg | Asp | Asn 555 |
| Glu | Asn | Arg | Val | Pro 560 | Thr | Cys | Glu | Glu | Val 565 | Met | Pro | Pro | Gln | Asn 570 |
| Leu | Glu | Arg | Ala | Asp 575 | Glu | Ile | Cys | Ile | Ala 580 | Gly | Ser | Pro | Leu | Thr 585 |
| Pro | Arg | Arg | Val | Thr 590 | Glu | Val | Arg | Ala | Asp 595 | Thr | Gly | Gly | Leu | Gly 600 |
| Arg | Ser | Ile | Thr | Ser 605 | Pro | Thr | Thr | Leu | Tyr 610 | Asp | Arg | Tyr | Ser | Ser 615 |
| Pro | Pro | Ala | Ser | Thr 620 | Thr | Arg | Arg | Arg | Leu 625 | Phe | Val | Glu | Asn | Asp 630 |
| Ser | Pro | Ser | Asp | Gly 635 | Gly | Thr | Pro | Gly | Arg 640 | Met | Pro | Pro | Gln | Pro 645 |
| Leu | Val | Asn | Ala | Val 650 | Pro | Val | Gln | Asn | Val 655 | Ser | Gly | Glu | Thr | Val 660 |
| Ser | Val | Thr | Pro | Val 665 | Pro | Gly | Gln | Thr | Leu 670 | Val | Thr | Met | Ala | Thr 675 |
| Ala | Thr | Val | Thr | Ala 680 | Asn | Asn | Gly | Gln | Thr 685 | Val | Thr | Ile | Pro | Val 690 |
| Gln | Gly | Ile | Ala | Asn 695 | Glu | Asn | Gly | Gly | Ile 700 | Thr | Phe | Phe | Pro | Val 705 |
| Gln | Val | Asn | Val | Gly 710 | Gly | Gln | Ala | Gln | Ala 715 | Val | Thr | Gly | Ser | Ile 720 |
| Gln | Pro | Leu | Ser | Ala 725 | Gln | Ala | Leu | Ala | Gly 730 | Ser | Leu | Ser | Ser | Gln 735 |
| Gln | Val | Thr | Gly | Thr 740 | Thr | Leu | Gln | Val | Pro 745 | Gly | Gln | Val | Ala | Ile 750 |
| Gln | Gln | Ile | Ser | Pro 755 | Gly | Gly | Gln | Gln | Lys 760 | Gln | Gly | Gln | Ser 765 |
| Val | Thr | Ser | Ser | Ser 770 | Asn | Arg | Pro | Arg | Lys 775 | Thr | Ser | Ser | Leu | Ser 780 |
| Leu | Phe | Phe | Arg | Lys 785 | Val | Tyr | His | Leu | Ala 790 | Ala | Val | Arg | Leu | Arg 795 |
| Asp | Leu | Cys | Ala | Lys 800 | Leu | Asp | Ile | Ser | Asp 805 | Glu | Leu | Arg | Lys | Lys 810 |
| Ile | Trp | Thr | Cys | Phe 815 | Glu | Phe | Ser | Ile | Ile 820 | Gln | Cys | Pro | Glu | Leu 825 |
| Met | Met | Asp | Arg | His 830 | Leu | Asp | Gln | Leu | Leu 835 | Met | Cys | Ala | Ile | Tyr 840 |
| Val | Met | Ala | Lys | Val 845 | Thr | Lys | Glu | Asp | Lys 850 | Ser | Phe | Gln | Asn | Ile 855 |
| Met | Arg | Cys | Tyr | Arg | Thr | Gln | Pro | Gln | Ala | Arg | Ser | Gln | Val | Tyr |

-continued

| | | | | 860 | | | | 865 | | | | | 870 | |
|---|---|---|---|---|---|---|---|---|---|---|---|---|---|---|
| Arg | Ser | Val | Leu | Ile | Lys | Gly | Lys | Arg | Lys | Arg | Arg | Asn | Ser | Gly |
| | | | | 875 | | | | 880 | | | | | 885 | |
| Ser | Ser | Asp | Ser | Arg | Ser | His | Gln | Asn | Ser | Pro | Thr | Glu | Leu | Asn |
| | | | | 890 | | | | 895 | | | | | 900 | |
| Lys | Asp | Arg | Thr | Ser | Arg | Asp | Ser | Ser | Pro | Val | Met | Arg | Ser | Ser |
| | | | | 905 | | | | 910 | | | | | 915 | |
| Ser | Thr | Leu | Pro | Val | Pro | Gln | Pro | Ser | Ser | Ala | Pro | Pro | Thr | Pro |
| | | | | 920 | | | | 925 | | | | | 930 | |
| Thr | Arg | Leu | Thr | Gly | Ala | Asn | Ser | Asp | Met | Glu | Glu | Glu | Glu | Arg |
| | | | | 935 | | | | 940 | | | | | 945 | |
| Gly | Asp | Leu | Ile | Gln | Phe | Tyr | Asn | Asn | Ile | Tyr | Ile | Lys | Gln | Ile |
| | | | | 950 | | | | 955 | | | | | 960 | |
| Lys | Thr | Phe | Ala | Met | Lys | Tyr | Ser | Gln | Ala | Asn | Met | Asp | Ala | Pro |
| | | | | 965 | | | | 970 | | | | | 975 | |
| Pro | Leu | Ser | Pro | Tyr | Pro | Phe | Val | Arg | Thr | Gly | Ser | Pro | Arg | Arg |
| | | | | 980 | | | | 985 | | | | | 990 | |
| Ile | Gln | Leu | Ser | Gln | Asn | His | Pro | Val | Tyr | Ile | Ser | Pro | His | Lys |
| | | | | 995 | | | | 1000 | | | | | 1005 | |
| Asn | Glu | Thr | Met | Leu | Ser | Pro | Arg | Glu | Lys | Ile | Phe | Tyr | Tyr | Phe |
| | | | | 1010 | | | | 1015 | | | | | 1020 | |
| Ser | Asn | Ser | Pro | Ser | Lys | Arg | Leu | Arg | Glu | Ile | Asn | Ser | Met | Ile |
| | | | | 1025 | | | | 1030 | | | | | 1035 | |
| Arg | Thr | Gly | Glu | Thr | Pro | Thr | Lys | Lys | Arg | Gly | Ile | Leu | Leu | Glu |
| | | | | 1040 | | | | 1045 | | | | | 1050 | |
| Asp | Gly | Ser | Glu | Ser | Pro | Ala | Lys | Arg | Ile | Cys | Pro | Glu | Asn | His |
| | | | | 1055 | | | | 1060 | | | | | 1065 | |
| Ser | Ala | Leu | Leu | Arg | Arg | Leu | Gln | Asp | Val | Ala | Asn | Asp | Arg | Gly |
| | | | | 1070 | | | | 1075 | | | | | 1080 | |
| Ser | His | | | | | | | | | | | | | |

( 2 ) INFORMATION FOR SEQ ID NO:3:

( i ) SEQUENCE CHARACTERISTICS:
( A ) LENGTH: 6 amino acids
( B ) TYPE: amino acid
( D ) TOPOLOGY: linear ( x i ) SEQUENCE DESCRIPTION: SEQ ID NO:3:

Phe Tyr Lys Val Ile Glu
5

( 2 ) INFORMATION FOR SEQ ID NO:4:

( i ) SEQUENCE CHARACTERISTICS:
( A ) LENGTH: 6 amino acids
( B ) TYPE: amino acid
( D ) TOPOLOGY: linear ( x i ) SEQUENCE DESCRIPTION: SEQ ID NO:4:

Gln Asp Leu His Arg Asp
5

TUMOR SUPPRESSOR PROTEIN PRB2, RELATED GENE PRODUCTS, AND DNA ENCODING THEREFOR

FIELD OF THE INVENTION

This invention relates to a tumor suppressor protein (pRb2) of the retinoblastoma family which binds to the E1A transforming domain. The invention also concerns DNA encoding for pRb2 and related gene products.

Background of the Invention

Many types of human cancer are now believed to be caused by an imbalance of growth regulators within a cell. A decrease in negative control growth regulators and/or their deactivation can cause a cancerous condition. Further, an increase in positive control growth regulators can also cause a cancerous condition.

Since the identification of the first tumor suppressor gene, much effort in cancer research has been focused on the identification of new tumor suppressor genes and their involvement in human cancer. Many types of human cancers are thought to develop by a loss of heterozygosity of putative tumor suppressor genes not yet identified (Lasko et al., *Annu. Rev. Genetics*, 25, 281–296 (1991)) according to Knudson's "two-hit" hypothesis (Knudson, *Proc. Natl. Acad. Sci. USA*, 68, 820–823 (1971)).

One of the most studied tumor suppressor genes is the retinoblastoma susceptibility gene (rb), whose gene product (pRb) has been shown to play a key role in the regulation of cell division. In interphasic cells, pRb contributes to maintaining the quiescent state of the cell by repressing transcription of genes required for the cell cycle through interaction with transcription factors, such as E2F (Wagner et al, *Nature*, 352, 189–190 (1991); Nevins, *Science*, 258, 424–429 (1992); and Hiebert et al., *Genes Develop.*, 6, 177–185 (1992)). The loss of this activity can induce cell transformation as evidenced by the reversion of the transformed phenotype in pRb cells after replacement of a functional pRb (Huang et al., *Science* 242 1563–1565 (1988); Bookstein et al., *Science*, 247 712–715 (1990); and Sumegi et al., *Cell Growth Differ.*, 1, 247–250 (1990)).

Upon entrance into the cell cycle, pRb seems to be phosphorylated by cell cycle-dependent kinases (Lees et al,, *EMBO J.* 10 4279–4290 (1991); Hu et al., *Mol. Cell. Biol.*, 12 971–980 (1992); Hinds et al., *Cell*, 70 993–1006 (1992); Matsushime et al., *Nature*, 35 295–300 (1992)) which is thought to permit its dissociation from transcription factors and, hence, the expression of genes required for progression through the cell cycle. Noteworthily, the association of pRb with cell cycle regulators like cyclins and cell cycle-dependent kinases suggests a universal character to its function.

However, pRb involvement in human cancer has been restricted to a limited number of tumor types suggesting that this hypothetically universal function may be exerted by other gene products in a cell type-specific manner. Consistently, knock out of the rb gene in mice affects only specific cell types and after several days of embryonic development (Jacks et al., *Proc. Natl. Acad. Sci. USA*, 68, 820–823 (1992); Lee et al., *Nature*, 359 288–294 (1992); Clarke et al., *Nature*, 359 328–330 (1992)).

The ability of several transforming proteins from human DNA tumor viruses to activate cell proliferation has been a useful tool for the identification of cellular factors involved in the regulation of the cell cycle. Negative regulators of cell growth may thus be effective targets for inactivation by these viral proteins, as it occurs with the product of the retinoblastoma gene.

Adenovirus E1A, SV40 T antigen, and papillomavirus E7 are three viral proteins which have been found to bind to pRb. This binding is responsible for the release of transcription factors required for the expression of cell cycle genes (Nevins, *Science*, 258 424–429 (1992); Bandara et al., *Nature*, 351 494–497 (1991)).

A conserved motif found in the three viral proteins allows for interaction and complex formation with pRb (Moran, *Curr. Op. Gen. Dev.*, 3 63–70 (1993)). In the case of the adenovirus E1A protein, this motif is located in the transforming domain 2, which is required for growth activation. The pRb-related product p107 also binds in this region (Egan et al., *Mol. Cell. Biol.*, 8 3955–3959 (1988); Whyte et al., *Cell*, 56 67–75 (1989)).

Domain 2 is also the site of interaction of an additional E1A-binding protein, p130 (Giordano et al., *Oncogene*, 6 481–485 (1991)). This has led to the suggestion that p130 has a structural relationship to pRb and p107 (Moran, *Curr. Op. Gen. Dev.*, 3 63–70 (1993)).

The E1A-binding domain in pRb and p107 is a conserved region termed the "pocket region" (Kaelin et al., *Mol. Cell. Biol.*, 10 3761–3769 (1990); Ewin et al., *Cell*, 66 1155–1164 (1991)), and it is thought to play a primary role in the function of these proteins. The pocket is structurally formed by two regions A and B, which are conserved in pRb and p107 and separated by nonconserved spacers of different sizes in pRb and p107.

In addition to pRb and p107, there are other cellular E1A-binding proteins that have been identified by co-immunoprecipitation experiments using antibodies to E1A. These cellular proteins include the major polypeptides p300, p130, p60/cyclin A, and several other minor forms (Yee, et al., *Virology* 147 142–153 (1985); Harlow et al., *Mol. Cell. Biol.* 6 1579–1589 (1986); Giordano, et al., Cell 58 981–990 (1989); Giordano et al, *Science* 253 1271–1275 (1991)). Binding to the N-terminal region has been shown to be exclusive to p300 (Egan et al., *Mol. Cell, Biol.*, 8 3955–3959 (1988); Whyte et al., *Cell*, 56 67–75 (1989); Stein et al., *J. Virol.*, 64 4421–4427 (1990)), and pRb2 consistently failed to bind to this region. Both domains 1 and 2 of the E1A protein have been shown to be necessary for the E1A binding of the following set of proteins: pRb, p107, p60/ cyclin A, and p130 (Egan et al., *Mol. Cell. Biol.*, 8 3955–3959 (1988); Whyte et al., Cell, 56 67–75 (1989); Giordano et al. *Science* 253 1271-1275 (1991)). Furthermore, the E1A-928 mutant has been previously shown to bind to p107 and p60/cyclin A, but not to pRb and p130.

The association of pRb with transcription factors, such as E2F, occurs by interactions at the pocket region (Raychaudhuri et al., *Genes Develop.*, 5 1200–1207 (1991)) and, recently, p107 has also been shown to exert such a binding profile (Cao et al., *Nature*, 355 176–179 (1992)). Moreover, the pocket region is found mutated in several human cancers where a lack of function of the pRb protein is thought to be involved in the acquisition of the transformed phenotype (Hu et al., *EMBO J.*, 9 1147–1153 (1990)); Huang et al., 1990).

There is a need for identification and sequencing of new rb-related genes that may have an involvement in cell growth inhibition. Genes related to rb and their protein products that also have tumor suppressor activity in specific cell types are needed. However, identification and sequenc-

SUMMARY OF THE INVENTION

Figure 1:
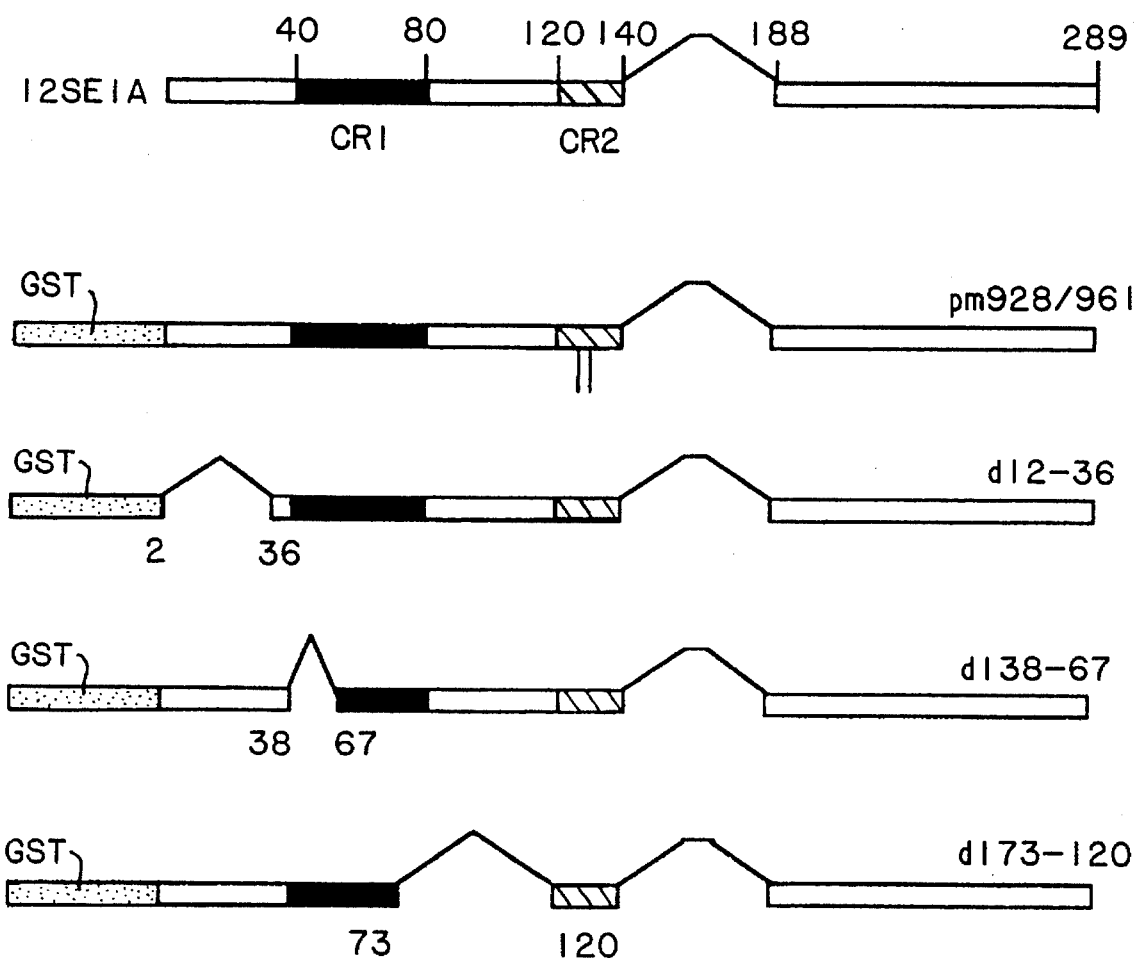
FIG. 1 is a schematic representation of wild type and mutant forms of the E1A protein. The mutant forms are pm928/961, d12-36, d138-67 and d173-120. The nature of each mutation is set forth schematically.

The present invention provides a recombinant DNA cloning vehicle comprising a cDNA sequence comprising the human pRb2 gene cDNA sequence. A preferred cDNA sequence is a sequence according to SEQ ID NO:1. The cDNA comprises a sequence coding for the amino acid sequence according to SEQ ID NO:2.

In another embodiment the present invention provides a protein essentially having an amino acid sequence according to SEQ ID NO:2. Preferably, the protein corresponding to SEQ ID NO:2 is not phosphorylated.

In a further embodiment the present invention provides a host cell line transformed by the cDNA of the cloning vehicle described above, which host cell line expresses the cDNA from the cloning vehicle to produce a protein. Preferably the cDNA has a sequence according to SEQ ID NO:i and the protein produced has a sequence according to SEQ ID NO:2.

DETAILED DESCRIPTION OF THE INVENTION

The pRb2 protein is a previously unsequenced, uncharacterized member of the pRb family of tumor suppressor proteins. This protein was designated as pRb2 since it binds to Adenovirus E1A protein in a manner similar to pRb and p107. Thus, the cDNA sequence coding for pRb2 was designated as the pRb2 gene.

Polymerase chain reaction (PCR) using probes derived from domains 1 and 2 of the rb gene was utilized to identify the pRb2 cDNA sequence as follows.

Synthetic degenerate oligonucleotides were designed based on conserved amino acid sequences flanking the spacers in pRb and p107. These oligonucleotides were designated as primer A and primer B and used as PCR primers to isolate and clone the pRb2 cDNA sequence.

Primer A is an oligonucleotide containing 18 nucleotides coding for the amino acid sequence Phe-Tyr-Lys-Val-Ile-Glu (SEQ ID NO:3). The 5' end of primer A also contains nine nucleotides which form a BamHI restriction site.

Primer B is an oligonucleotide containing 18 nucleotides coding for the amino acid sequence Gln-Asp-Leu-His-Arg-Asp (SEQ ID NO:4). The 5' end of primer B also contains nine nucleotides which form a HindIII restriction site.

Each of the 18-mer primers A and B correspond to conserved portions in the pocket regions of pRb and p107. The two restriction sites (BamHI for primer A, and HindIII for primer B) were used to conveniently subclone the amplified PCR fragments into a commercially available vector (pBluescript, Stratagene, La Jolla, Calif.).

The PCR product was used as a probe for the screening of cDNA libraries from human 293 and HeLa cells. From the screening several positive clones were identified. These clones were sequenced and analyzed for a clone containing full length cDNA.

One of the HeLa cDNA clones contained a putative initiation codon which is compatible with the Kozak initiation sequence (Kozak, *J. Mol, Biol.*, 196 947–950 (1987). This clone showed a unique open reading frame ending in a termination codon 3,249 base pairs downstream (see SEQ ID NO:1). The complete sequence included 55 base pairs upstream of the open reading frame which did not contain any putative initiation site, and a 3' noncoding region ending in a poly A tail. The open reading frame encoded a polypeptide of 1,082 amino acids (SEQ ID NO:2) with a predicted molecular mass of approximately 120 kD. This cDNA clone was designated rb2 and, hence, the encoded protein pRb2.

The sequence of protein pRb2 (SEQ ID NO:2) as compared to the pRb and p107 protein sequences shows a high level of identity, 53% with respect to p107, and 32% with respect to pRb. This suggests a closer relationship of pRb2 to p107. A partial comparisons of the amino acid sequences of these three proteins shows that the pocket region is clearly conserved in pRb2, mainly at the level of the domains A and B. This suggests that pRb2 has properties similar to pRb and p107, such as the formation of cell cycle-associated protein complexes which are known to occur via the pocket region. This suggests that pRb2 would be involved in the cell cycle machinery. Moreover, the high identities found in the C and N-terminal portions between pRb2 and p107 suggest a role for these regions in a function of p107 and pRb2 which may differentiate them from pRb.

The pRb2 cDNA clone was transcribed into an RNA segment in vitro by a T7 RNA polymerase capping reaction on the linearized pBluescript-pRb2. The resulting transcription product (RNA segment) was extracted with a phenol/chloroform solution and precipitated in an ethanol solution.

The transcription product was used as a substrate for in vitro translation into a protein by using a rabbit reticulocyte lysate (Promega, Biotec, Madison, Wis.) and $^{35}$S-methionine as a radioactive label (Pelham et al., *Eur. J. Biochem.*, 6.7 248–256 (1976)). Several truncated forms of the protein were produced. The largest pRb2 protein form migrated to approximately 120 kD by SDS-PAGE. The most prominent of the bands corresponds to a protein form which migrated to around 90 kD, and a third protein form was found to migrate to 85 kD.

After isolation, the 120 kD pRb2 protein and its 90 kD and 85 kD truncated forms were tested for E1A protein binding properties. The E1A binding results were compared to the E1A binding properties of the pRb and p107 proteins. Both pRb and p107 proteins bind to the adenovirus E1A protein through their respective pocket regions. Demonstration of E1A protein binding by the pRb2 protein would indicate that the latter protein has a key role in the regulation of cell division. The E1A binding capacity of pRb2 was thus determined as follows.

Wild type and mutant forms of the E1A protein were obtained. The nature of the mutations are set forth in FIG. 1. A binding assay was performed to test the binding of the wild type and mutant E1A proteins to in vitro-translated pRb2 protein (120 kD and truncated 90 kD and 85 kD proteins) precleared of translation solution. Each of the three in vitro translated main forms of the pRb2 protein bound to E1A.

An E1A deletion mutation involving the N-terminal portion of E1A (d12-36) did not affect binding of the pRb2 to E1A. The binding of pRb2 was also not affected by deletion mutations involving the transforming domain 1 of E1A (E1A mutants d138-67 and d173-120). This suggests that binding of pRb2 to E1A does not take place via these regions of E1A. However, the ability of the pRb2 protein to bind was almost completely abolished when an E1A mutant protein containing a double point mutation in the transforming domain 2 of E1A was used (E1A mutant pm928/961, in which Cys was substituted for Gly at position 124, and Lys for Glu at position 135). Therefore, the transforming domain 2 of E1A is required for binding to pRb2. This suggests that the E1A-binding capacity of pRb2 is involved, at least in part, in the transforming activity of E1A.

Although the pRb2 protein is similar in molecular weight to the p130 protein and they both have similar binding profiles to E1A wild type and mutant proteins the two proteins are not identical. The p130 protein is phosphorylated on Ser and Thr residues while pRb2 is unphosphorylated. Moreover, p130 exists in more than one phosphorylated form.

A cloning vector designated as pBluescript-pRb2 which contained the pRb2 cDNA was deposited with the ATCC, Rockville, Md. on Aug. 11, 1993 and was given the ATCC number 15521.

An *E. coli* bacterial strain designated as *E. coli* pBluescript-pRb2 which contained a plasmid containing the pRb2 cDNA was deposited with the ATCC, Rockville, Md. on Aug. 11, 1993 and given the ATCC number 69383.

It is well within the skill of those in the genetic engineering art to use the nucleotide sequence of SEQ ID NO:i or related sequences encoding for the pRb2 protein of the present invention to produce pRb2 protein via microbial processes. Using the nucleotide sequence of SEQ ID NO:i to produce pRb2 is made easier for one of ordinary skill by utilizing the pBluescript-pRb2 cloning vector according to the invention.

Fusing the nucleotide sequences encoding for the pRb2 protein into an expression vector and transforming or transfecting into hosts, either eukaryotic (yeast or mammalian cells) or prokaryotic (bacterial cells), are standard procedures used in producing other well-known proteins, e.g., insulin, interferons, human growth hormone, and the like. Similar procedures, or obvious modifications thereof, can be employed to prepare pRb2 proteins by microbial means or mammalian tissue-culture technology in accord with the subject invention.

Those of ordinary skill in the art will appreciate the fact that the cDNA fragment set forth in SEQ ID NO:I is only one DNA segment coding for pRb2. Other equivalent DNA segments of substantial similarity will immediately be envisioned which will code for pRb2. The present invention also includes such equivalent DNA sequences.

Moreover, substitution of equivalent amino acids in SEQ ID NO:2 would not be expected to affect the pRb2 protein's activity. These amino acid substitutions would be envisioned by those of ordinary skill in the art. Such equivalent amino acid sequences are also included within the present invention.

The following non-limiting examples are provided to illustrate the invention.

EXAMPLES

EXAMPLE 1: Obtaining pRb2 cDNA and Amino Acid Sequences

A. Synthesis of PCR Primers

Primers A and B were synthesized using standard oligonucleotide synthesis techniques and purified.

Primer A contained 18 nucleotides coding for the polypeptide sequence according to SEQ ID NO:3. The 5'-end was of nine additional nucleotides that formed a BamHI restriction site. Primer B contained 18 nucleotides coding for the polypeptide sequence according to SEQ ID NO:4. The 5'-end was of nine additional nucleotides which formed a HindIII restriction site.

B. PCR Amplification of a Human 293 cDNA Library

A lambda-ZAPII cDNA library was obtained from reverse transcription of RNA from human 293 cells using standard techniques. The cDNA library was amplified via PCR with Primers A and B from Example 1A above. The PCR was performed using a GeneAmp™ kit (Perkin Elmer Cetus, Norwalk, Conn.) according to the instructions of the manufacturer. Briefly, thirty cycles including a one minute denaturization at 94° C., one minute annealing at 37° C., and two minutes extension at 68° C., were followed by fifteen minute extension. This resulted in PCR amplification of a 1kb fragment in addition to pRb and p107 segments.

C. Subcloning and Nucleotide Sequencing the 1kb Fragment

The amplified 1kb fragment was subcloned into a pBluescript vector (Stratagene). After subcloning, nucleotide sequencing was performed using the dideoxy method of the Sequenase kit (United States Biochemicals). The nucleotide sequence of the 1kb fragment revealed some homology with pRb and p107 cDNAs.

D. Probing cDNA Libraries From 293 and HeLa Cells

The 1kb fragment was utilized as a probe to screen additional cDNA libraries. Lambda-ZAPII cDNA libraries from human 293 and HeLa cells (Stratagene), respectively were screened using the 1kb fragment labeled with $\alpha$-$^{32}$P-CTP by the random primer method (Boehringer Mannheim). Briefly, lambda-ZAP phage was adsorbed to *Escherichia coli* BB4 strain bacteria and plated in agar medium. Nitrocellulose filters were hybridized to the PCR probe in a high stringency protocol which included the pre-hybridization mixture: 5x SSPE, 10x Denhardt's solution, 150 µg/ml herring sperm DNA, 50% formamide and 2% SDS; a hybridization mixture adding $10^e$ cpm/ml of the 1kb PCR probe to the pre-hybridization mixture; and, three washes of twenty minutes each at 42° C. with 0.2x SSC and 0.1% SDS.

E. Analyzing the Positive Clones From the Probing

From the probing procedures of Example 1D several positive clones were located. In vivo excision (Stratagene) was performed on the several positive Lambda-ZAP clones. pBluescript vectors containing cDNA clones were obtained. The cDNA clones were reproduced and nucleotide sequencing of each cDNA clone was performed as described above in Example 1C. The sequencing results analyzed for the full length cDNA including the 1kb fragment.

One of the HeLa cDNA clones contained a putative initiation codon which was compatible with the Kozak initiation sequence. This clone showed a unique open reading frame ending in a termination codon 3,249 base pairs downstream (see SEQ ID NO:1). The complete sequence included 55 base pairs upstream of the open reading frame which did not contain any putative initiation site, and a 3' non-coding region ending in a poly A tail. The open reading frame encoded a polypeptide of 1,082 amino acids (SEQ ID NO:2) with a predicted molecular mass of approximately 120 kD. This cDNA clone was designated rb2 and, hence, the encoded protein pRb2. The pBluescript vector cloned with the pRb2 gene was designated as pBluescript-pRb2.

The sequence of protein pRb2 (SEQ ID NO:2, which is derived from the corresponding cDNA sequence) as compared to pRb and p107 protein sequences showed a high level of identity, 53% with respect to p107, and 32% with respect to pRb. This suggests a closer relationship of pRb2 to p107. Partial comparisons of these three protein sequences show that the pocket region is clearly conserved in pRb2, mainly at the level of the domains A and B.

EXAMPLE 2: E1A Binding of In Vitro-Translated pRb2

A. Transcription and Translation of pBluescript-pRb2

The Example 1E pBluescript-pRb2 cDNA clone was transcribed into an RNA segment in vitro by a T7 RNA polymerase capping reaction on the linearized pBluescript-pRb2. The resulting transcription product (RNA segment) was extracted with a phenol/chloroform solution and precipitated in an ethanol solution.

The transcription product RNA segment was used as a substrate for in vitro translation into a protein by using a rabbit reticulocyte lysate (Promega, Biotec, Madison, Wis.) and $^{35}$S-methionine as a radioactive label (Pelham et al., Eur. J. Biochem., 67 248–256 (1976)). Several truncated forms of the protein were produced. The largest form migrated to approximately 120 kD by SDSPAGE. The most prominent of these bands migrated to around 90 kD, and a third one was found to migrate to 85 kD.

B. Obtaining Wild-Type and Mutant E1A Proteins

Wild type and mutant forms of the E1A protein were obtained. The mutant forms were pm928/961, d12-36, d138-67 and d173-120. The nature of the mutations are set forth in FIG. 1. The wild type and mutant forms of E1A were sub-cloned into pGEX-2T and expressed in E. coli as GST-fusion proteins. The E1A proteins were then isolated from E. coli cultures by standard techniques.

C. Binding Assay for pRb2 and E1A Proteins

A binding assay was performed to test the binding of the wild type and mutant E1A proteins of Example 2B with the in vitro-translated pRb2 proteins of Example 2A precleared of translation solution. The pRb2 protein (120 kD, 90 kD, and 85 kD) was precleared with glutathione-sepharose and GST-glutathione-sepharose beads in NETN buffer containing 1 mM DTT, 1 mM PMSF, and 10 µg/ml leupeptine, at 4° C.

Two µg of each E1A protein were incubated with precleared pRb2 for one hour at 4° C., and glutathionesepharose beads were added and incubated for an additional hour. Proteins were resolved using SDS-PAGE according to standard protocols and a Fuji phosphoimage analyzer system was used to develop the protein signal.

Figure 2:
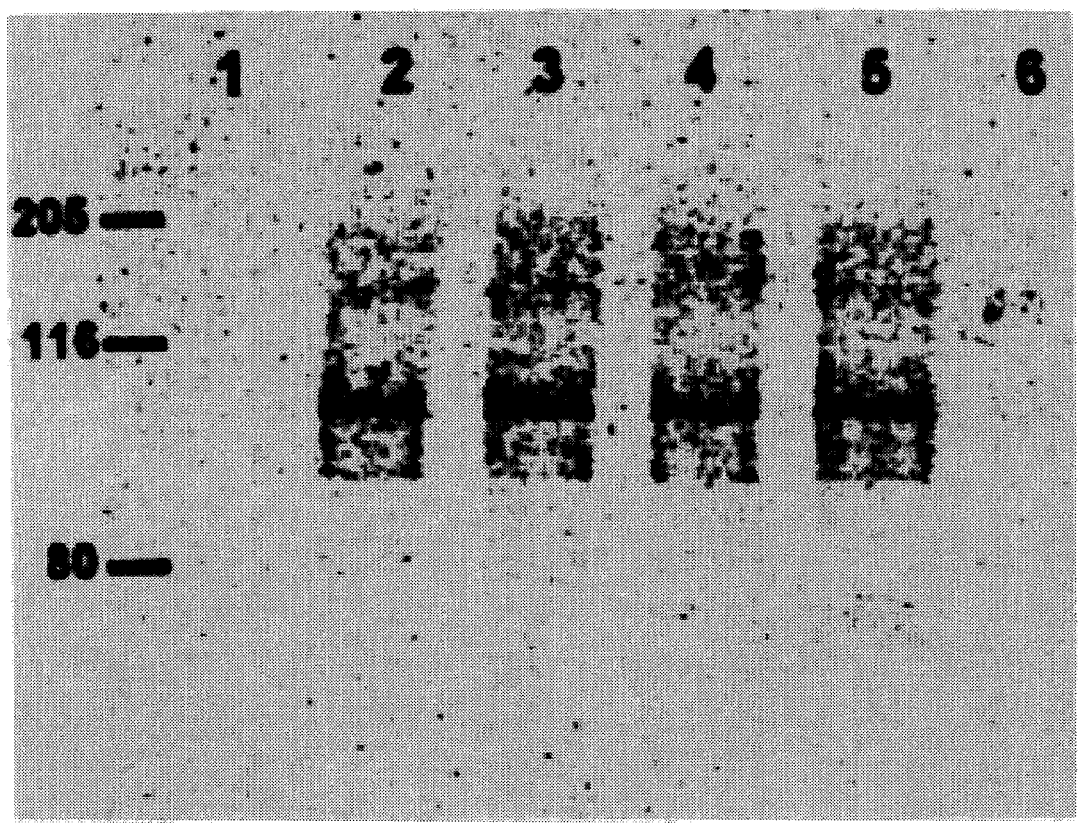
FIG. 2 is an SDS-PAGE gel showing binding of the pRb2 protein to a fusion construct of a wild-type E1A protein and a Glutathione-S-Transferase (GST) protein (lane 2) and to E1A mutant constructs fused to a GST protein: d12-36 (lane 3), d138-67 (lane 4), d173-120 (lane 5), and pm928/961 (lane 6). GST protein with no E1A fused was included as a control (lane 1), which showed no binding with the pRb2 protein.

The results of the binding assay are set forth in FIG. 2, which is an SDS-PAGE showing binding to wild-type E1A (lane 2) and to E1A mutant constructs: d12-36 (lane 3), d138-67 (lane 4), d173-120 (lane 5), and pm928/961 (lane 6). GST with no E1A fused was included as a control (lane 1). The in vitro-translated product resulting from a rabbit reticulocyte translation reaction with no exogenous RNA was included as a control, which did not give any signal (not shown).

Each of the three in vitro translated main forms of the pRb2 protein (120 kD, 90 kD, and 80 kD) bound to E1A. A deletion mutation involving the N-terminal portion of E1A (d12-36) did not affect pRb2 binding. E1A binding to pRb2 was not affected by d138-67 or d173-120 deletion mutations, both involving the transforming domain 1 of E1A. This suggests that binding of pRb2 to E1A does not take place in these regions. However, binding was almost completely abolished when an E1A-fusion protein containing a double point mutation in the transforming domain 2 of E1A was used (E1A mutant pm928/961, in which Cys was substituted for Gly at position 124, and Lys for Glu at position 135). Therefore, the transforming domain 2 of E1A is required for binding to pRb2. This suggests that the E1A-binding capacity of pRb2 is involved, at least in part, in the transforming activity of E1A.

For comparative purposes the pRb and p107 proteins were obtained and a binding assay performed with the wild type and mutant E1A proteins. The pRb2 protein showed similar binding characteristics to the pRb and p107 proteins.

Since the pRb2 protein binds the E1A protein in manner similar to the pRb protein, the pRb2 protein is a useful diagnostic tool for identifying cells infected with adenovirus E1A or a related DNA virus producing oncoproteins related to the E1A protein. Because of the binding capacity of pRb2, it can also be administered to cells infected with adenovirus E1A, where it may act as a cell growth suppressor to reverse the effects of the E1A oncoprotein. This reversal of E1A protein effects could restore the balance of cell growth in a retinoblastoma cancer tumor. Thus, pRb2 may be a useful tumor suppressor agent, for treating cancers such as retinoblastoma interocular cancer. Further, pRb2 may be a useful research tool for binding and identifying other DNA tumor virus oncoproteins which have sequences related to the E1A protein.

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indicating the scope of the invention.

I claim:

1. A heterologous cloning vector comprising DNA encoding human pRb2 having the amino acid sequence SEQ ID NO:2.

2. A cloning vector according to claim 1 wherein the DNA sequence comprises the DNA sequence SEQ ID NO:1.

3. A cloning vector according to claim 1 which is ATCC No. 75521.

4. Purified and isolated DNA encoding human pRb2 having the amino acid sequence SEQ ID NO:2.

5. Purified and isolated DNA according to claim 4, which DNA has the nucleotide sequence SEQ ID NO:i.

6. A host cell line transformed by the cloning vector of claim 1, which host cell line expresses the DNA from the cloning vector to produce a protein with the amino acid sequence SEQ ID NO:2.

7. A host cell line according to claim 6, wherein the expressed DNA has a sequence according to SEQ ID NO:1.

8. A host cell line of claim 18 which is *E. coli* bacteria strain ATCC No. 69383.

* * * * *